US006479290B1

(12) United States Patent
Mehtali et al.

(10) Patent No.: US 6,479,290 B1
(45) Date of Patent: Nov. 12, 2002

(54) CHIMERIC ADENOVIRAL VECTORS

(75) Inventors: Majid Mehtali, Amsterdam (NL); Monika Lusky, Frieburg (DE); Arend Jan Winter, Strasbourg (FR)

(73) Assignee: Transgene S. A., Strasbourg (FR)

( * ) Notice: Subject to any disclaimer, the term of this patent is extended or adjusted under 35 U.S.C. 154(b) by 0 days.

(21) Appl. No.: 09/463,486

(22) PCT Filed: May 27, 1999

(86) PCT No.: PCT/FR99/01238

§ 371 (c)(1),
(2), (4) Date: Jan. 27, 2000

(87) PCT Pub. No.: WO99/61638

PCT Pub. Date: Dec. 2, 1999

(30) Foreign Application Priority Data

May 27, 1998 (FR) .............................. 98 06654

(51) Int. Cl.[7] ..................... C12N 15/861; C12N 15/86; C12N 7/01; C12N 15/09; C07H 21/04
(52) U.S. Cl. ................. 435/457; 435/235.1; 435/320.1; 435/91.33; 435/91.4; 435/455; 536/23.1
(58) Field of Search ............................ 435/320.1, 91.4, 435/235.1, 325, 455, 6, 91.1, 91.33, 457; 536/23.1

(56) References Cited

U.S. PATENT DOCUMENTS 5,707,618 A * 1/1998 Armentano et al. ..... 424/93.21

FOREIGN PATENT DOCUMENTS

| FR | 2 707 664 A | 1/1995 |
| WO | 97 45550 | 12/1997 |

OTHER PUBLICATIONS

Ghush–Choudhury G. et al, "Human Adenovirus Cloning Vectors Based On Infectious Bacterial Plasmids", Gene, vol. 50, No. 1/03, Jan. 1, 1986, pp. 161–171, XP002004335, p. 170.

Reddy et al, "Nucleotide sequence, genome organization and transcription map of bovin adenovirus type 3", Journal of Virology, vol. 72, No. 2, Feb. 1998, pp. 1394–1402, XP002087289, p. 1396.

Mittal et al, "Development of a bovine adenovirus type 3–based expression vector", Journal of General Virology, vol. 76, 1995, pp. 93–102, XP002087288.

* cited by examiner

*Primary Examiner*—David Guzo
*Assistant Examiner*—Gerald G. Leffers, Jr.
(74) *Attorney, Agent, or Firm*—Burns, Doane, Swecker & Mathis, L.L.P.

(57) ABSTRACT

The invention concerns adenoviral vectors having the characteristic of containing a region essential for heterologous packaging with respect to the adenoviral genome from which they are derived. The invention also concern a method for making a viral preparation containing said adenoviral vectors, a cell, a pharmaceutical composition or material comprising them and their therapeutic or prophylactic use. Finally, the invention concerns an adenoviral genome of animal origin having attenuated packaging properties with respect tot he native genome from which it is derived.

35 Claims, No Drawings

CHIMERIC ADENOVIRAL VECTORS

BACKGROUND OF THE INVENTION

The present invention relates to novel adenoviral vectors which have the characteristic of containing a region essential for encapsidation which is heterologous with respect to the adenoviral genome from which they are derived. These vectors may be used as helper or recombinant vectors, the former allowing propagation of the latter. The subject of the invention is also a method for preparing a viral preparation containing said adenoviral vectors, a cell, a pharmaceutical composition or a composition of material comprising them as well as their use for therapeutic or prophylactic purposes. Finally, the present invention also relates to an adenoviral genome of animal origin having attenuated encapsidation capacities compared with the native genome from which it is derived. The ainvention is of especial interest in the perspectives of gene therapy especially in humans.

DESCRIPTION OF THE RELATED ART

Gene therapy is defined as the transfer of genetic information into a host cell or organism. The first protocol applied to humans was initiated in the United States in September 1990 on a patient who was genetically immunodeficient because of a mutation affecting the gene encoding Adenine Deaminase (ADA). The relative success of this first experiment encouraged the development of this technology for various diseases including both genetic (with the aim of correcting the dysfunction of a defective gene) and acquired (cancers, infectious diseases such as AIDS and the like) diseases. Most of the current strategies use vectors to carry the therapeutic gene to its cellular target. Many vectors including viral and synthetic vectors have been developed during the past few years and have been the subject of many publications accessible to persons skilled in the art.

The importance of adenoviruses as gene therapy vectors has already been mentioned in many prior art documents. They infect many cell types, both dividing and quiescent cells, are nonintegrative and not very pathogenic. In addition, they possess a natural tropism for the respiratory tracts. These specific properties make adenoviruses vectors of choice for many therapeutic and even vaccine applications. As a guide, their genome consists of a linear and double-stranded DNA molecule of about 36 kb which carries about thirty genes involved in the viral cycle. The early genes (E1 to E4; E for early) are divided into 4 regions dispersed in the genome. The E1, E2 and E4 regions are essential for viral replication whereas the E3 region, which is involved in modulating the anti-adenovirus immune response in the host, is not. The late genes (L1 to L5; L for late) encode predominantly the structural proteins and partially cover the early transcription units. They are for the most part transcribed from the Major Late Promoter MLP. In addition, the adenoviral genome carries, at its ends, cis-acting regions which are essential for encapsidation, consisting of inverted terminal repeats (ITR) situated at the 5' and 3' ends and an encapsidation region which follows the 5' ITR.

The adenoviral vectors which are currently used in gene therapy protocols lack the major part of the E1 region in order to avoid their dissemination in the environment and in the host organism. Additional deletions in the E3 region make it possible to increase the cloning capacities. The genes of interest are introduced into the viral DNA in place of one or other of the deleted regions. While the feasibility of transferring genes using these so-called first-generation vectors is now well established, the question of their safety remains. In addition to the risk of generating replication-competent particles, the potential immunogenecity of the viral proteins still expressed can, in some specific applications, prevent the persistence of the transduced cells and the stable expression of the transgene. These disadvantages have justified the construction of new-generation vectors. They conserve the regions in cis (ITRs and encapsidation sequences) which are essential for encapsidation but comprise additional genetic modifications aimed at suppressing the in vivo expression of most of the viral genes (see for example International Application Wo 94/28152). In this regard, a so-called minimal vector, which is deficient for all the adenoviral functions, represents an alternative of choice.

The techniques for preparing adenoviral vectors are widely described in the literature. In a first instance, the genome is prepared by homologous recombination in the 293 line (see in particular Graham and Prevect, 1991, Methods in Molecular Biology, Vol 7, Gene Transfer and Expression Protocols; Ed E. J. Murray, The Human Press Inc, Clinton, N.J.) or in *Escherichia coli* (see for example International Application WO 96/17070). It is then necessary to propagate the vector in order to constitute a stock of viral particles containing it. This production step is critical and should make it possible to obtain high infectious particle titers to be able to envisage a large-scale development for the purpose of the preparation of clinical batches. Complementation lines providing in trans the viral products of expression for which the vector is defective are used to this effect. For example, the viruses deleted for E1 can be propagated in the 293 line which is established from human embryonic kidney cells (Graham et al., 1977, J. Gen. Virol. 36, 59–72). As regards the secondgeneration vectors, it is possible to use lines complementing two essential viral functions, such as those described by Yeh et al. (1996, J. Virol. 70, 559–565), Krougliak and Graham (1995, Human Gene Therapy 6, 1575–1586), Wang et al. (1995 Gene Therapy 2, 775–783), Lusky et al. (1998, J. Virol. 72, 2022–2033) and in International Applications WO 94/28152 and WO 97/04119. Because of the potential toxicity of the viral products of expression, these lines need to be optimized in terms of growth capacity and viral particle yield before envisaging their use in an industrial process. Furthermore, a line complementing all the adenoviral functions, suitable for the propagation of the minimal vectors is currently not yet available.

Another alternative is based on the use of an additional viral element designated "helper virus" to complement, at least in part, the defective functions of a recombinant adenoviral vector. The helper viruses of the prior art consist of an adenoviral genome, optionally deleted for an essential region for which the recombinant vector does not require complementation. By way of example, cotransfection into the 293 line of an E1$^-$ helper virus and of an E1$^-$E4$^-$ recombinant adenoviral vector leads to the formation of viral particles of recombinant vector. The E1 function is provided by the 293 line and the E4 function by the helper virus.

However, a major disadvantage of this method is that the cells produce a mixed population of viral particles, some comprising the recombinant vector and others the helper vector. In practice, the preparations predominantly contain helper viral particles, these having a selective advantage, such that the contamination may reach and even exceed 90% . The presence of the helper virus is not desirable in the context of a therapy applied to humans and, because of this, requires the use of physical separation techniques, such as ultracentrifugation.

DETAILED DESCRIPTION OF THE INVENTION

The present invention proposes exploiting the respective growth properties of the human and animal adenoviruses. The inability of bovine BAV3 adenoviruses to be propagated in a human line has now been demonstrated whereas Ad5 can be propagated in bovine cells. Indeed, the infection by BAV3 adenoviruses, alone or in the presence of Ad5, in the human 293 line does not lead to the formation of infectious BAV3 viral particles. On the other hand, Ad5 virions are obtained by infecting a bovine line. In addition, there is no expression of BAV3 viral proteins in human cells.

On the basis of these observations, the present invention proposes in particular a system of encapsidation occurring in two stages and using adenoviruses which are chimeras between Ad5 and BAV3. There has now been constructed (i) a helper vector derived from an Ad5 genome in which the native encapsidation region is replaced by that of the bovine BAV3 adenovirus and (ii) a recombinant defective adenoviral vector derived from an Ad5 and comprising two encapsidation regions, the first of Ad5 origin (autologous) and the second of BAV3 origin (heterologous). The transfection of the two vectors into a bovine cell line infected with a BAV3 adenovirus leads to the amplification of the three viral genomes and to the production of viral particles of the three types. During this first amplification stage, the BAV3 genome provides the in trans-acting factors allowing the encapsidation of the recombinant and helper vectors and the latter at least partially complements the defective functions of the recombinant vector. The mixture of the three types of virus is recovered from the bovine cells and used to infect human 293 cells. The BAV3 genome and the helper vector possessing only one encapsidation region derived from BAV3 cannot be propagated in the human line even in the presence of Ad5 because of the absence of the encapsidation factors recognizing the BAV3 sequences, which excludes the formation of corresponding viral particles. However, the helper vector can produce in trans the factors necessary for the encapsidation of the recombinant vector mediated by the encapsidation signal of Ad5 origin and complement, in association with the 293 cells, the defective early and late functions, with the aim of predominantly generating virions containing the recombinant vector. The present invention meets safety objectives by considerably reducing the contamination of the adenoviral preparations by the helper vectors and thus avoids the use of long and expensive separation techniques of varying efficiency.

Accordingly, the subject of the present invention is an adenoviral vector derived from an adenoviral genome, characterized in that it comprises a region essential for encapsidation which is heterologous with respect to the adenoviral genome from which it is derived.

For the purposes of the present invention, an adenoviral vector is obtained from a parental adenovirus whose genome is modified. A minimal modification is the insertion of a region essential for encapsidation of a different origin (heterologous). Of course, other modifications may also be envisaged. These may be of various types (deletion, addition, substitution of one or more nucleotides) and may be located in coding regions of the adenoviral genome or outside these (regions involved in the expression of the viral genes, in the encapsidation and the like) and may be affected both in the early and late regions. In this regard, an adenoviral vector which is particularly suitable for the present invention is defective, that is to say is incapable of being autonomously propagated in a host cell in the absence of complementation. It may be defective for one or more viral genes which are essential for replication. These genes may be deleted (as a whole or in part), made nonfunctional (for example by mutation) or substituted by other sequences (in particular by a gene of interest whose expression is sought in a host cell or organism).

The adenoviral vector of the present invention may be derived from a human or animal adenovirus and of any serotype. The subgroup C human adenoviruses and in particular the adenoviruses 2 (Ad2) and 5 (Ad5) are most particularly suitable for carrying out the invention. Among the animal adenoviruses which can be used in the context of the present invention, there may be mentioned canine, avian, bovine, murine, ovine, porcine and simian adenoviruses and the like. As a guide, it is possible to use the murine adenoviruses Mav1 (Beard et al., 1990, Virology 175, 81–90), the canine adenoviruses CAV-1 or CAV-2 (Spibey and Cavanagh, J. Gen. Virol., 1989, 70, 165–172; Linne, 1992, Virus Research 23, 119–133; Shibata et al., 1989, Virol. 172, 460–467; Jouvenne et al., Gene, 1987, 60, 21–28), the avian adenoviruses DAV (Zakharchuk et al., Arch. Virol., 1993, 128, 171–176) or the bovine adenoviruses BAV3 (Mittal et al., J. Gen. Virol., 1995, 76, 93–102). In general, the abovementioned adenoviruses are available in collections and in particular at the ATCC and have been the subject of many studies published in the prior art. As regards adenovirus 5 (Ad5), it should be noted that the complete sequence of its genome is available from GenBank under accession number M73260. This sequence is fully incorporated by reference into the present application.

For the purposes of the present invention, "region essential for encapsidation" is understood to mean a region acting in cis to ensure, in collaboration with protein factors, in particular viral protein factors, the encapsidation of a viral vector genome into a viral capsid. Such regions consist in particular, in the case of the adenoviral genome, of the 5' and 3' ITRs, and the encapsidation region. These terms are well known in the field of the art considered.

The characteristic of the adenoviral vector according to the invention is that it carries a region essential for encapsidation which is heterologous, that is to say of a different origin, with respect to the parental adenovirus. Although it may be derived from any virus (retrovirus, poxvirus and the like), an adenoviral origin is preferred as long as it is an adenovirus of a genus or serotype which is different from the parental adenovirus. Preferably, according to the present invention, said heterologous region essential for encapsidation consists of the encapsidation sequence and optionally of at least one of the 5' and 3' ITRs.

Depending on the origin of the adenovirus, the regions essential for encapsidation may vary somewhat. However, they can be identified on the basis of the available sequence data or by analogy with human adenoviruses. The ITRs are naturally located at the 5' and 3' ends of the adenoviral genome and are involved in the stages of replication and encapsidation of said genome. Generally, the ITRs comprise between 100 and 200 base pairs. Numerous ITR sequences are proposed in the literature; there may be mentioned by way of example Hearing et al., 1987, J. Virol., 61, 2555–2558 for Ad5 or WO 95/16048 for BAV3. The encapsidation region (noted Ψ) is located behind the 5' ITR of the adenoviral genome and comprises repetitive motifs which participate in the encapsidation. For example, that of Ad5 comprises 7 motifs designated AI to AVII having the consensus sequence 5' A/T AN A/T TTTG 3' (where N represents any nucleotide) and situated at positions 241–248, 262–269, 304–311, 314–321 and 339–346 of the viral genome (Grable and Hearing, 1990, J. Virol. 64, 2047–2056; Schmid and Hearing, 1998, J. Virol. 72, 6339–6347). The encapsidation regions of various adenoviruses are described in the literature (see for example Hammarskjold and Winberg, 1980, Cell 20, 787–795 for Ad16; Hearing et al., 1987, J. Virol. 61, 2555–2558 for Ad5; Robinson and Tibbets, 1984, Virology, 137, 276–286 for Ad3; Shibata et al., 1989, Virology 172, 460–467 for CAV2; WO 95/16048 for BAV3). Purely by way of illustration, it should be mentioned that the encapsidation region of Ad5 extends at least from the nucleotides (nt) 240 to 350. As for that of BAV3, it is contained in a fragment of 0.3 kb between the positions about 185 to about 514. However, the limits of the encapsidation region can vary and shorter or longer regions are also suitable. Persons skilled in the art are capable of isolating a fragment of the 5' end of an adenoviral genome, of inserting it into an appropriate vector and of verifying its encapsidation capacities in an appropriate line, for example by determining the viral titer or the expression of a reporter gene.

The sequences carrying the heterologous region essential for encapsidation may be isolated from a viral genome by conventional means (digestion with a restriction enzyme, PCR and the like) or may be produced by chemical synthesis. Optionally, in the context of the present invention, they may comprise rotations (deletion, substitution and/or addition of one or more nucleotides) compared with the native sequences. It is also possible to include other exogenous sequences (restriction sites and the like). They may be inserted into the adenoviral vector according to the invention in addition to the autologous region or as a replacement thereof. The insertion may take place in 5' or in 3' of the autologous region, in its place or at a different site (for example at the 3' end just before the 3' ITR).

Advantageously, the adenoviral vector according to the invention is derived from an adenovirus of human origin and the heterologous region essential for encapsidation from an adenovirus of animal oriain. In this regard, a vector which is most particularly suitable for the present invention is derived from a subgroup C human adenovirus and, in particular from an adenovirus 2 (Ad2) or 5 (Ad5) . As for the heterologous region essential for encapsidation, it is preferably derived from an animal adenovirus selected from those mentioned above.

According to a completely preferred embodiment, the adenoviral vector according to the invention is derived from an Ad5 and the heterologous region essential for encapsidation from a bovine adenovirus, in particular from a BAV3.

It should be mentioned that the abovementioned embodiments are preferred but that other combinations may be used in the context of the present invention. It is possible, for example, to envisage an adenoviral vector derived from an Ad5 and comprising a heterologous region essential for encapsidation derived from another human adenovirus of a different serotype (Ad3, Ad7 and the like). Alternatively, the adenoviral skeleton may be of animal origin and the region essential for encapsidation derived from a human adenovirus.

As indicated above, the adenoviral vector according to the invention is preferably defective at least for the E1 function. Such a deficiency may be obtained by total or partial deletion of the corresponding region. Many E1⁻ vectors are described in the prior art and may be used in the context of the present invention. In addition, it may comprise additional mutations/deletions affecting one or more other viral genes, in particular in the E2, E4 and/or L1–L5 regions. Any combination may be envisaged (E1⁻ E2⁻, E1⁻ E4⁻, E1⁻ E2⁻ E4⁻ and the like) . Such vectors are in particular described in International Application WO 94/28152. To illustrate these embodiments, there may be mentioned the heat-sensitive mutation affecting the DBP (for DNA Binding Protein) gene of the E2A region (Ensinger et al., 1972, J. Virol. 10, 328–339). A partial deletion of the E4 region, with the exception of the sequences encoding the open reading frames (ORF) 6 and 7, may also be envisaged (Ketner et al., 1989, Nucleic Acids Res. 17, 3037–3048). Another possibility is the total deletion of the transcriptional unit E4. Moreover, the adenoviral vector according to the invention may lack all or part of the nonessential region E3. According to this alternative, it may be advantageous to conserve, nevertheless, the E3 sequences encoding the polypeptides allowing escape from the immune system of the host, in particular the glycoprotein gp19k (Gooding et al., 1990, Critical Review of Immunology 10, 53–71). In some applications (recombinant vector), the nonfunctionality of all the viral genes is preferred.

According to a first variant, the adenoviral vector according to the invention may be used as helper viral vector to complement all or part of the defective functions of a recombinant adenoviral vector. According to an advantageous embodiment, it is defective at least for the E1 function. Optionally, it may be defective for additional functions such as E2. Persons skilled in the art are capable of defining the required deficiencies depending on the recombinant vector which it is sought to complement and the chosen cell line. It should be mentioned that the E4 function may be provided by only ORF 6 and 7. The presence of all or part of the E3 region is optional. According to a specific embodiment, it comprises the 5' and 3' ITR sequences and the sequences encoding the E2, E4 and/or L1–L5 functions derived from a human adenovirus, in particular from an Ad5, and a heterologous encapsidation region derinted from a bovine adenovirus, in particular from a BAV3. According to another embodiment, the helper viral vector comprises the sequences encoding the E2, E4 and/or L1–L5 functions derived from a human adenovirus, in particular from an Ad5 and heterologous 5' ITR sequences, 3' ITR sequences and encapsidation region which are derived from a bovine adenovirus, in particular from a BAV3.

A helper adenoviral vector according to the invention is obtained by insertion, into an adenoviral genome as defined above, of at least one heterologous region essential for encapsidation. A preferred manner of proceeding is to replace the autologous region essential for encapsidation with the heterologous region. Persons skilled in the art are capable of producing such a construct by applying conventional molecular biology techniques.

According to a second variant, the adenoviral vector according to the invention is a recombinant adenoviral vector and comprises at least one gene of interest placed under the control of elements necessary for its expression in a host cell or organism.

The gene of interest used in the present invention may be derived from a eukaryotic organism, from a prokaryote, from a parasite or from a virus other than an adenovirus. It may be isolated by any technique conventionally used in the field of the art, for example by cloning, PCR or chemical synthesis. It may be of the genomic type (comprising all or part of the introns as a whole), of the complementary DNA type (cDNA, lacking introns) or of the mixed type (minigene). Moreover, it may encode an antisense RNA and/or a messenger RNA (mRNA) which will then be translated into a polypeptide of interest, it being possible for the latter to be (i) intracellular, (ii) incorporated into the membrane of the host cell or (ii) secreted. It may be a polypeptide as found in nature (native), a portion thereof (truncated), a mutant exhibiting in particular improved or modified biological properties or alternatively a chimeric polypeptide obtained from the fusion of sequences of various origins.

Within the context of the present invention, it may be advantageous to use a gene of interest which encodes a cytokine (α, β or γ interferon, interleukin (IL), in particular IL-2, IL-6, IL-10 or IL-12, a tumor necrosis factor (TNF), a colony-stimulating factor (GM-CSF, C-CSF, M-CSF, etc.), a cell receptor (in particular recognized by the HIV virus), a receptor ligand, a coagulation factor, a growth factor (FGF, standing for Fibroblast Growth Factor, VEGF, standing for Vascular Endothelial Growth Factor), an enzyme (urease, renin, thrombin, metalloproteinase, NOS, standing for Nitric Oxide Synthetase, SOD, catalase, etc.), an enzyme inhibitor (xl-antitrypsin, antithrombin III, viral protease inhibitor, PAI-1, standing for plasminogen activator inhibitor), a class I or II major histocompatibility complex antigen or a polypeptide which acts on the expression of the corresponding genes, a polypeptide which is able to inhibit a viral, bacterial or parasitic infection or its development, a polypeptide which reacts positively or negatively on apoptosis (Bax, Bcl2, BclX, etc.), a cytostatic agent (p21, p16, Rb), an apolipoprotein (ApoAI, ApoAIV, ApoE, etc.), an angiogenesis inhibitor (angiostatin, endostatin, etc.), a marker (β-galactosidase, luciferase, etc.) or any other gene of interest which has a therapeutic effect on the targeted ailment. More precisely, for the purpose of treating an hereditary malfunction, use will be made of a functional copy of the defective gene, for example a gene encoding factor VIII or IX within the context of A or B hemophilia, dystrophin within the context of Duchenne's and Becker's myopathies, insulin within the context of diabetes, and the CFTR (Cystic Fibrosis Transmembrane Conductance Regulator) protein within the context of cystic fibrosis. As regards inhibiting the initiation or progress of tumors or cancers, preference will be given to using a gene of interest which encodes an antisense RNA, a ribozyme, a cytotoxic product (herpes simplex virus 1 thymidine kinase (HSV-1-TK), ricin, cholera or diphtheria toxin, product of the FCY1 and FUR1 yeast genes encoding uracil phosphoribosyl transferase and cytosine deaminase, etc.), an antibody, an inhibitor of cell division or transduction signals, an expression product of a tumor suppressor gene (p53, Rb, p73, etc.), a polypeptide which stimulates the immune system, a tumor-associated antigen (MUC-1, BRCA-1, early or late antigens (E6, E7, L1, L2, etc.) of an HPV papilloma virus, etc.) where appropriate in combination with a cytokine gene. Finally, use can be made, within the context of an anti-HIV therapy, of a gene which encodes an immunoprotective polypeptide, an antigenic epitope, an antibody (2F5; Buchacher et al., 1992, Vaccines 92, 191–195), the extracellular domain of the CD4 receptor (sCD4; Traunecker et al., 1988, Nature 331, 84–86), an immunoadhesin (for example a CD4-IgG immunoglobulin hybrid; Capon et al., 1989, Nature 337, 525–531; Byrn et al., 1990, Nature 344, 667–670), an immunotoxin (for example fusion of the antibody 2F5 or the immunoadhesin CD4-2F5 to angiogenin; Kurachi et al., 1985, Biochemistry 24, 5494–5499), a transdominant variant (EP 0614980, WO 95/16780), a cytotoxic product such as one of those mentioned above, or else an α or β IFN.

Moreover, one of the genes of interest may also be a selectable gene which makes it possible to select or identify the transfected or transduced cells. There may be mentioned the neo gene (encoding neomycin phosphotransferase), which confers resistance to the antibiotic G418, the dhfr (Dihydrofolate Reductase) gene, the CAT (Chloramphenicol Acetyl Transferase) gene, the pac (Puromycin Acetyl mransferase) gene or the gpt (Xanthine Guanine Phosphoribosyl Transferase) gene. In general, the selectable genes are known to persons skilled in the art.

The phrase "elements necessary for the expression" designates the genetic elements allowing the transcription of a gene of interest into RNA and the translation of an mRNA into a polypeptide. Among these, the promoter is of particular importance. It may be isolated from any gene of eukaryotic or even viral origin and may be constitutive or regulatable. Alternatively, it may be the natural promoter of the gene an question. Moreover, it may be modified so as to improve the promoter activity, suppress a region which inhibits transcription, make a constitutive promoter regulatable or vice versa, introduce a restriction site and the like. There may be mentioned, by way of examples, the eukaryotic promoters of the PGK (Phospho Glycerate Kinase), MT (metallothionein; McIvor et al., 1987, Mol. Cell. Biol. 7, 838–848), α1-antitrypsin, CFTR, surfactant, immunoglobulin, β-actin (Tabin et al., 1982, Mol. Cell. Biol. 2, 426–436) or SRα (Takebe et al., 1988, Mol. Cell. Biol. 8, 466–472) genes, the SV40 virus (Simian Virus) early promoter, the RSV (Rous Sarcoma Virus) LTR, the HSV-1-TK promoter, the CMV virus (Cytomegalovirus) early promoter and the adenoviral promoters E1A and MLP. It may also be a promoter which stimulates expression in a tumor or cancer cell. There may be mentioned in particular the romoters of the MUC-1 gene which is overexpressed in reast and prostate cancers (Chen et al., 1995, J. lin. Invest. 96, 2775–2782), the CEA (for carcinoma embryonic antigen) gene which is overexpressed in colon cancers (Schrewe et al., 1990, Mol. Cell. Biol. 10, 2738–2748), the tyrosinase gene which is overexpressed in melanomas (Vile et al., 1993, Cancer Res. 53, 3860–3864), the ERB-2 gene which is overexpressed in cancers of the breast and of the pancreas (Harris et al., 1994, Gene Therapy 1, 170–175) and the α-fetoprotein gene which is overexpressed in liver cancers (Kanai et al., 1997, Cancer Res. 57, 461–465). The Cytomegalovirus (CMV) early promoter is most particularly preferred.

The elements necessary for the expression may, in addition, include additional elements which improve the expression of the gene of interest or its maintenance in the host cell. There may be mentioned in particular the intron sequences, signal sequences for secretion, nuclear localization sequences, internal sites for reinitiation of translation of the IRES type, poly A sequences for termination of transcription, tripartite leaders and replication origins. These elements are known to persons skilled in the art.

When the recombinant adenoviral vector according to the invention comprises several genes of interest, these may be placed under the control of the same genetic elements (polycistronic cassette using an internal site for initiation of translation of the IRES type for reinitiating the translation of the second cistron) or of independent elements.

A particularly advantageous embodiment consists in a recombinant adenoviral vector comprising a second region essential for encapsidation which is autologous with respect to the adenoviral genome from which it is derived. In other words, it carries two encapsidation regions, one autologous and the other heterologous. Their position in the adenoviral vector is unimportant. They may be placed in particular at one of the ends or separated at each of the ends of said vector. Advantageously, the heterologous region is placed in 3' of the autologous region.

Within the context of the present invention, a recombinant adenoviral vector according to the invention is defective for the E1 function and at least one of the E2, E4 and/or L1—L5 functions. A preferred example is provided by a vector defective for all the adenoviral functions (minimum vector) which comprises, in addition to the gene(s) of interest, at least the 5' and 3' ITRs and an autologous region essential for encapsidation derived from a human adenovirus, in particular from an Ad5 and a heterologous region essential for encapsidation derived from a bovine adenovirus, in particular from a BAV3.

It is within the capability of persons skilled In the art to generate a recombinant adenoviral vector according to the invention by molecular biology techniques. They will obviously know how to adapt the technology as a function of the specific data (type of vector, gene of interest and the like).

The present invention also relates to the use of a helper adenoviral vector according to the invention for complementing all or part of the defective functions of a replication-defective recombinant adenoviral vector, in particular of a recombinant adenoviral vector according to the invention, said helper and recombinant vectors both being derived from the same adenovirus and, in particular from an Ad5, and said heterologous regions essential for encapsidation carried by the helper vector and, optionally, the recombinant vector being derived from the same adenovirus different from the preceding one and in particular from a BAV3.

The present invention also relates to a composition comprising:
(a) a helper adenoviral vector according to the invention,
(b) a replication-defective recombinant adenoviral vector, in particular a recombinant adenoviral vector according to the invention, and
(c) optionally, an adenoviral genome which is derived from an animal adenovirus of the same origin as the heterologous regions essential for encapsidation carried by the helper and recombinant vectors a) and optionally b).

The present invention also relates to an adenoviral genome which is derived from an animal adenovirus, in particular from a bovine adenovirus and, in particular, from a BAV3, characterized in that it has an attenuated encapsidation capacity compared with the adenovirus from which it is derived. The attenuation is intended to reduce the propagation of the adenoviral genome to the benefit of a genome carrying a native region (helper and recombinant adenoviral vector according to the invention). It may be obtained by partial deletion of the encapsidation region or by mutation of one or more motifs controlling the encapsidation process. An example of attenuation is provided in International Application WO 94/28152 and in Imler et al. (1995, Human Gene Therapy 6, 711–721). Persons skilled in the art know the techniques which make it possible to verify the attenuation, for example by determining the viral titer (Graham and Prevec, 1991, supra) or the expression of a reporter gene with respect to an equivalent virus carrying a native region essential for encapsidation. An attenuated region essential for encapsidation exhibits an encapsidation efficiency which is reduced by a factor of 2 to 1000, advantageously of 3 to 100 and, preferably, of 5 to 50.

The animal adenoviral genome according to the invention may be replication-competent or may comprise modifications affecting one or more viral genes, such as those cited above. In particular, the total or partial deletion of the E1 region of said genome may be advantageous within the context of the present invention. It should be mentioned that the genome and/or the vectors may be in the form of DNA or of a virus.

The present invention also relates to a method for preparing a viral preparation comprising a replication-defective recombinant adenoviral vector, in particular a recombinant adenoviral vector according to the invention, according to which:
(a) there are introduced into a first cell line
   (i) a helper adenoviral vector according to the invention,
   (ii) an adenoviral genome which is derived from an animal adenovirus, and
   (iii) said recombinant adenoviral vector,
said adenoviral genome (ii) being of the same origin as the heterologous regions essential for encapsidation which are carried by the vectors (i) and optionally (iii) and said adenoviral genome (ii) and the vectors (i) and (iii) being capable of replicating in said first cell line,
(b) said first cell line is cultured under appropriate conditions to allow the production of viral particles comprising the vectors (i) and (iii) and the adenoviral genome (ii),
(c) said viral particles obtained in step b) are recovered from the cell culture,
(d) a second cell line is infected with said viral particles recovered in step c), said helper vector (i) and said adenoviral genome (ii) having a zero or reduced encapsidation and/or replication capacity in said second cell line,
(e) said second cell line is cultured under appropriate conditions to allow the encapsidation of said recombinant adenoviral vector (iii) and produce said viral preparation, and
(f) said viral preparation obtained in step e) is recovered from the cell culture.

For the purposes of the present invention, the adenoviral vectors and genomes may be introduced by any prior art means into the first cell line, in particular by transfection and/or infection. It is possible to transfect the vectors into the line which is infected with particles of animal adenoviral genome (prior to, subsequent to or concomitant with the transfection). The viruses containing the various elements (i), (ii) or (iii) may be prepared according to prior art techniques. Moreover, said replication-defective recombinant adenoviral vector may consist of a vector as described in WO 94/28152, WO 94/08026, WO 93/19191 or WO 94/12649.

Moreover, the genome (ii) may be of the wild type, according to the invention (attenuated) and/or comprise one or more modifications affecting the functionality of one or more viral genes.

According to an advantageous embodiment, the first cell comprises
(i) a helper adenoviral vector which is defective at least for the E1 function, derived from a human adenovirus (in particular from an Ad5) and carrying a heterologous region essential for encapsidation derived from a bovine adenovirus (in particular from a BAV3),
(ii) an adenoviral genome derived from a bovine adenovirus (in particular from a BAV3), optionally according to the invention, and
(iii) a recombinant adenoviral vector which is defective for the E1 function and at least one of the E2, E4 and/or L1–L5 functions and carrying a second autologous encapsidation region as defined above, derived from a human adenovirus (in particular from an Ad5) and carrying a heterologous region essential for encapsidation derived from a bovine adenovirus (in particular from a BAV3), said first cell line being of bovine origin.

According to a completely advantageous embodiment, the defective helper adenoviral vector in question in (i) of the methods described above comprises a heterologous region essential for encapsidation derived from a bovine adenovirus (in particular from a BAV3) which comprises the 5' and 3' ITRs and the encapsidation region.

Alternatively, it is possible to use an adenoviral genome (ii) which is defective for the E1 function. As regards the preferred variant, a BAV3 genome which is defective for the E1 function is described in International Application WO 95/16048. In this case, use will be made of a first cell line capable of complementing the E1 function of said adenoviral genome of animal origin. A line of the same animal origin as said adenoviral genome (ii) will be preferably used. It may be an established line or a primary line.

The term complementation cell is standard in the field of the art. Within the context of the present invention, it refers to a eukaryotic cell capable of providing in trans at least part of the defective functions of an adenoviral vector or genome according to the invention. In general, a cell for complementing an adenoviral function may be obtained by transfecting the corresponding viral genes into an appropriate cell line. All the standard means for introducing a DNA into a cell may be used (transfection with calcium phosphate, electroporation, microinjection, lipofection, protoplast fusion and the like). Moreover, the viral genes are carried by conventional vectors (synthetic, viral or plasmid vectors and the like) and placed under the control of elements allowing their constitutive or regulated expression in said complementation cell. The complementation lines appropriate for the adenoviral vectors are known to persons skilled in the art (see for example International Application WO 94/28152, WO 97/04119 and Graham et al., J. Gen. Virol., 1977, 36: 59–72).

A particularly suitable bovine line is derived from an MDBK line (ATCC CCL-22 or CRL-6071) or from primary cells, in particular of the retina or of fetal kidney, and comprises the sequences encoding the E1 region of a bovine adenovirus, and in particular of a BAV3, which are placed under the control of the elements necessary for their expression in said line.

According to a preferred embodiment, the second cell line is a cell for complementing the E1 function of a human adenovirus, in particular of an Ad5. Use will be preferably made of the 293 line. However, other lines such as those described in Application WO 94/28152 may also be used.

The viral particles of step c) and the viral preparation may be recovered from the culture supernatant but also from the cells. One of the methods commonly used consists in lysing the cells by successive freeze/thaw cycles in order to recover the virions from the lysis supernatant. These may then be amplified and purified according to prior art techniques (chromatographic method, ultracentrifugation in particular through a cesium chloride gradient, and the like).

The present invention also relates to the viral preparation obtained according to the method according to the invention. According to an advantageous embodiment, it comprises at least 30% of infectious viral particles containing the recombinant adenoviral vector according to the invention. Advantageously, it comprises at least 50%, preferably at least 70%, and most preferably at least 80% of said particles.

The present invention also relates to a host cell comprising an adenoviral vector according to the invention or infected with a viral preparation according to the invention. A mammalian cell, and in particular a human cell, is most particularly suitable. It may comprise said vector in a form integrated into the genome or otherwise (episome). It may be a primary or tumor cell of a hematopoietic origin (totipotent stem cell, leukocyte, lymphocyte, monocyte or macrophage and the like), muscle cell (satellite cell, myocyte, myoblast and the like), cardiac, pulmonary, tracheal, hepatic, epithelial or fibroblast cell.

The present invention also relates to a cell comprising:
(i) a helper adenoviral vector according to the invention,
(ii) an adenoviral genome which is derived from an animal adenovirus, and
(iii) a replication-defective recombinant adenoviral vector, in particular a recombinant adenoviral vector according to the invention.

Said cell is preferably a cell for complementing an adenoviral function and, in particular, the E1 function of an animal or human adenovirus. It has the characteristics defined above.

The present invention also relates to a pharmaceutical composition comprising, as therapeutic or prophylactic agent, an adenoviral vector, a viral preparation or a host cell according to the invention in combination with a pharmaceutically acceptable carrier. The composition according to the invention is more particularly intended for the preventive or curative treatment of diseases by gene therapy and applies to both genetic diseases (hemophilia, diabetes, cystic fibrosis, Duchenne's or Becker's myopathy, autoimmune diseases) and acquired diseases (cancers, tumors, cardiovascular diseases, diseases of infectious origin such as hepatitis B or C, AIDS and the like).

A pharmaceutical composition according to the invention may be manufactured in a conventional manner for administration by the local, parenteral or digestive route. In particular, a therapeutically effective quantity of the therapeutic or prophylactic agent is combined with a pharmaceutically acceptable carrier. The routes of administration which may be envisaged are many. There may be mentioned, for example, the intragastric, subcutaneous, intracardiac, intramuscular, intravenous, intraarterial, intraperitoneal, intratumor, intranasal, intrapulmonary or intratracheal route. For the latter three embodiments, administration by aerosol or instillation is advantageous. The administration may be made as a single dose or as a dose which is repeated once or several times after a certain time interval. The appropriate route of administration and dosage vary as a function of various parameters, for example the individual or the disease to be treated or the gene(s) of interest to be transferred. The viral preparation according to the invention may be formulated in the form of doses of between $10^4$ and $10^{14}$ pfu (plaque forming units), advantageously $10$ and $10^{13}$ pfu, and preferably $10^6$ and $10^{12}$ pfu. As regards the recombinant adenoviral vector according to the invention, doses comprising 0.01 to 100 mg of DNA, preferably 0.05 to 10 mg and most preferably 0.5 to 5 mg may be envisaged. The formulation may also include a pharmaceutically acceptable diluent, adjuvant or excipient. It may be provided in liquid or dry form (lyophylizate and the like).

The viral vector or preparation according to the invention may be optionally combined with one or more substances which improve the transfection efficiency and/or the stability. These substances are widely documented in the literature which is accessible to persons skilled in the art (see, for example, Felgner et al., 1987, Proc. West. Pharmacol. Soc.

32, 115–121; Hodgson and Solaiman, 1996, Nature Biotechnology 14, 339–342; Remy et al., 1994, Bioconjugate Chemistry 5, 647–654). By way of nonlimiting illustration, they may be polymers, lipids, in particular cationic lipids, liposomes, nuclear proteins or neutral lipids. These substances may be used alone or in combination.

Finally, the present invention relates to the use of an adenoviral vector, of a viral preparation or of a host cell according to the invention for the transfer and the expression of a gene of interest in a host cell or organism. A preferred use consists in the treatment of the human or animal body by gene therapy or immunotherapy. According to a first possibility, the medicament may be administered directly in vivo (for example by intravenous injection into an accessible tumor, into the lungs by aerosol and the like). It is also possible to adopt the ex vivo approach which consists in collecting cells from the patient (bone marrow stem cells, peripheral blood lymphocytes, muscle cells and the like), transfecting or infecting them in vitro according to prior art techniques and readministering them to the patient. The preferred use is for the preparation of a medicament intended for the treatment of diseases by gene therapy or immunotherapy.

The invention also extends to a method of treatment according to which a therapeutically effective quantity of a recombinant adenoviral vector, of a viral preparation or of a host cell according to the invention is administered to a patient requiring such a treatment.

EXAMPLES

The present invention is illustrated by the following examples without being limited as a result.

The constructs described below are produced according to general genetic engineering and molecular cloning techniques which are detailed in Maniatis et al., (1989, Laboratory Manual, Cold Spring Harbor, Laboratory Press, Cold Spring Harbor, N.Y.) or according to the manufacturer's recommendations when a commercial kit is used. The homologous recombination steps are preferably carried out in the *E. coli* strain BJ 5183 (Hanahan, 1983, J. Mol. Biol. 166, 557–580). As regards the repair of the restriction sites, the technique used consists in filling the protruding 5' ends with the aid of the large fragment of DNA polymerase I of *E. coli* (Klenow). Moreover, the adenoviral genome fragments used in the various constructs described below are precisely indicated according to their position in the nucleotide sequence of the Ad5 and BAV3 genome, as disclosed in the GeneBank data bank under the reference M73260 and AF030154 respectively.

As regards the cell biology, the cells are transfected or transduced and cultured according to standard techniques well known to persons skilled in the art. In the examples which follow, use is made of the cell lines 293 (Graham et al., 1977, supra; available from ATCC under the reference CRL1573) and MDBK (ATCC CRL-6071 or CCL-22). It is understood that other cell lines can be used.

Example 1

Absence of Multiplication of the BAV3 Viruses in the Human Lines

The human line MDBK and the human lines A549 (ATCC CCL-185), HeLa (ATCC CCL-2) and 293 (ATCC CRL-1573) are infected with a wild-type BAV3 virus at different MOIs (1, 2 and 10). The cells are harvested 3 days after the infection and the viral titers determined on the permissive MDBK cells. The multiplication factor is less than 1 in the case of the infection of the human cells whereas it is between 50 and 100 for the bovine line. These results indicate the inability of the BAV3 vector to be propagated in the human lines.

The expression of the viral genes of BAV3 is verified by reverse PCR after infection of the BAV3 virus into established human lines (A549, HeLa, 293, MRC5, RPMI) or primary human lines (primary muscle line PHM). The control line consists of the MDBK line. The cells are recovered and the polyA+ RNAs are isolated according to conventional technique. The reverse transcription is carried out with an antisense primer specific for the E1 region and followed by PCR amplification with the same primer and a sense primer specific for E1. The PCR products are subjected to Southern blot Analysis and detected with a probe specific for E1 which makes it possible to detect a band of 626 bp corresponding to the genomic DNA and of 519 bp derived from the polyA+mRNA. In the MDBK cells, an expression of the viral E1 gene which is maximal 16 hours after the infection is observed. E1 is also expressed in the 293 line. On the other hand, no expression of E1 mRNA can be detected in all the other human lines tested.

These results show that the human cells are infected with the BAV3 virus but that the latter cannot replicate therein.

Example 2

Construction of Chimeric Adenoviral Vectors Ad5/BAV3

A vector is first of all constructed which comprises a cassette for expressing the bacterial LacZ gene encoding β-galactosidase. To do this, the XhoI-SalI fragment of pTG8595 (Lusky et al., 1998, J. Virol. 72, 2022–2033) carrying the LacZ coding sequences is cloned into the XhoI site of the plasmid pCI (Promega). The latter is a eukaryotic expression vector comprising the CMV promoter, splicing sequences, multiple cloning sites and the SV40 polyA sequence. The cassette for expressing the LacZ gene, flanked by the abovementioned regulatory elements, is isolated in the form of a BglII-BamHI fragment and introduced into the BglII site of the transfer vector pTG8343, to give pTG6452. As a guide, the transfer vector comprises the 5' end of Ad5 deleted for the majority of the E1 sequences (nt 1 to 458 and 3329 to 5788), inserted into a plasmid ppolyII (Lathe et al., 1987, Gene 57, 193–201). The adenoviral genome is reconstituted by homologous recombination between the PacI-NsiI fragment obtained from pTG6452 and the vector pTG3652 carrying the Ad5 genome deleted for the E3 region, cleaved by the enzyme ClaI. The vector thus obtained, called pTG6481, contains the Ad5 sequences lacking the E1 region (nt 459 to 3328) and the E3 region (nt 28249 to 30758) and the pCMV-LacZ-pA SV40 cassette cloned in place of the E1 region. The encapsidation region is of Ad5 origin.

The next step is to insert the encapsidation region of BAV3 into the preceding vector. Two sites of insertion were tested: the first upstream of the native encapsidation region, at the level of the AflIII site at position 151 of the Ad5 genome and the other downstream thereof at the level of the SalI site (at position 451 of Ad5). The first construct pTG6466 is generated by AflIII digestion of PTG6452, treatment with Klenow and introduction of the HaeII-PvuII fragment of 844 bp covering the sequences at positions 141 to 984 of the BAV3 genome, this fragment having being subjected beforehand to the action of Klenow. The vector pTG6467 is generated according to the same protocol, except that pTG6452 is linearized with SalI. Thus, the vectors pTG6466 and pTG6467 contain two encapsidation regions, one of Ad5 origin and the other of BAV3 origin (about 0.8 kb).

A reduced BAV3 encapsidation region derived from the preceding one by ThaI or BstuI digestion (positions 185 to 514 of the BAV3 genome) was also used. As above, the BAV3 region of about 0.3 kb is inserted into the Ad5 recombinant vectors either at the level of the AflIII site (in 5' of the autologous psi region) or at the level of the SalI site (in 3' of the autologous psi region). In the latter case, the transfer vector pTG6458 is generated and the adenoviral genome is reconstituted by homologous recombination as above to give pTG6482.

A construct is then generated in which the Ad5 encapsidation region is exchanged against its BAV3 homologue. The vector pTG6452 is digested with AflIII (nt 151) and SalI (nt 451) and then treated with Klenow polymerase. The fragment of 300 bp carrying the Ad5 encapsidation region is replaced with the HaeII-PvuII fragment (844 bp) isolated from BAV3 and made blunt by the action of Klenow. pTG6468 is obtained which carries the sole BAV3 encapsidation region in an Ad5 context. An identical construct uses the BAV3 encapsidation region of 0.3 kb.

The modified regions are reintroduced into the adenoviral genome by homologous recombination as indicated above.

In an identical manner, a helper adenoviral vector derived from the Ad5 genome comprising the encapsidation region and the 5' and 3' ITRs of BAV3 was constructed. For that, the vector pTG13373 which is derived from the Ad5 genome deleted for the E1 and E3 regions is constructed, comprising the 5' ITR and the encapsidation region of 0.3 kb of the BAV3 genome.

The vector pTG 13373 is obtained by replacing the 5' ITR and the Ad5 encapsidation region which are present in pTG 8343 with the 5' ITR and the BAV3 encapsidation region which are present in pTG 5431; as a guide, pTG 5431 consists of the 5' end (nucleotides 1 to 8217) of the BAV3 genome. To do this, pTG 8343 is digested with BglII, subjected to the action of Klenow, and then digested with PacI, and pTG 5431 is digested with AccI, treated with Klenow, and digested with PacI. The fragments thus obtained are linked to give pTG 13372. Finally, pTG 13373 is obtained by homologous recombination between the fragments obtained from pTG 13372, digested with BglI, and from pTG 6401 digested with PacI.

The vector pTG 14310 derived from the Ad5 genome deleted for the E1 and E3 regions and comprising the 5' and 3' ITRs as well as the BAV3 encapsidation region is then obtained in the following manner.

The Ad5 3' ITR in the vector pTG 13384 (consisting of the 3' end (nucleotides 32800 to 35935) of the Ad5 genome; a cloning cassette being inserted between nucleotides 35826 and 35827) is replaced with the BAV3 3' ITR. To do this, pTG 13384 is digested with XbaI, subjected to the action of Klenow, and then digested with PacI. Moreover, pTG 5451 is digested with ApoI, treated with Klenow, and digested with PacI. As a guide, the vector pTG 5451 comprises the 5' end (nucleotides 1 to 1651 deleted for the 829–1077 fragment) and the 3' end of BAV3 (nucleotides 33232 to 34446) separated by a unique HindIII restriction site. The fragments thus obtained are linked to give pTG 14261.

Moreover, the recircularization of pTG 14261 after digestion with XbaI and BamHI and action of Klenow allows the elimination of the HindIII cleavage site upstream of the bovine ITR of pTG 14261. The vector pTG 14262 is thus obtained.

In parallel, pTG 13373 digested with HindIII is recircularized in order to obtain pTG 14263 which contains the 5' ITR and the encapsidation sequence of 0.3 kb of BAV3 as well as the 3' ITR of Ad5.

The Ad5 3' ITR in the vector pTG 14263 is then replaced with the BAV3 3' ITR of pTG 14262. To do this, pTG 14263 and pTG 14262 are digested with HindIII and PacI. The fragments thus obtained are linked to give pTG 14266.

Finally, the adenoviral genome is reconstituted by homologous recombination between pTG 14266 linearized with HindIII and pTG 13373 digested with PacI. The vector obtained, called pTG 14310, is derived from the genome of Ad5 deleted for the E1 and E3 regions and contains the 5' and 3' ITRs as well as the BAV3 encapsidation region.

An adenoviral genome similar to that of pTG 14310, but comprising a BAV3 encapsidation region of 0.8 kb, was also obtained. For that, the 5' ITR and the encapsidation region of Ad5 which are present in pTG 8343 were replaced with the 5' ITR and the encapsidation region of 0.8 kb of BAV3 which are present in pTG 5431. To do this, pTG 8343 is digested with BglII, subjected to the action of Klenow and then digested with PacI. On the other hand, pTG 5431 is digested with PvuII and PacI. The fragments thus obtained are linked to give pTG 14313.

The 5' ITR and the encapsidation region of 0.3 kb of BAV3 which are present in pTG 14266 are then replaced with the 5' ITR and the encapsidation region of 0.8 kb of BAV3 which are present in pTG 14313. To do this, a homologous recombination is carried out between the SspI/MfeI fragment obtained from pTG 14266 and the ScaI/NsiI fragment obtained from pTG 14313. The vector thus obtained is called pTG 14315.

Finally, the adenoviral genome is reconstituted by homologous recombination between the HindIII fragment obtained from pTG 14315 and the PacI fragment obtained from pTG 6401. The vector thus obtained, called pTG 14316, is derived from the Ad5 genome and comprises the 5' and 3' ITRs as well as the encapsidation region of 0.8 kb of BAV3.

An additional example of a vector according to the invention consists in a vector which is derived from the Ad5 genome deleted for the E1 and E3 regions and containing the 5' and 3' ITRs as well as the encapsidation region of 0.3 kb of BAV3, in which the encapsidation region has been inserted just upstream of the 3' ITR.

To construct such a vector, the BAV3 encapsidation region in pTG 13372 and in pTG 14266 is first of all deleted. For that, pTG 13372 is digested with AflIII, subjected to the action of Klenow and then digested with PacI, and pTG 14262 is digested with PvuII and PacI. The fragments thus obtained are linked to give pTG 14311.

The deletion of the bovine encapsidation region of pTG 14266 is obtained by homologous recombination between the XmnI/DraIII fragment obtained from pTG 14266 and the PvuI/SphI fragment obtained from pTG 14311. The vector pTG 14328 is then obtained.

The Ad5 3' ITR in pTG 13384 is then replaced with the 3' ITR and the encapsidation sequence of 0.3 kb of BAV3 which are present in pTG 5431. For that, pTG 13384 is digested with BamHI, subjected to the action of Klenow and then digested with PacI. On the other hand, pTG 5431 is digested with AflIII, treated with Klenow and digested with PacI. The fragments thus obtained are linked to give pTG 14271.

The introduction of the BAV3 encapsidation sequence just upstream of the 3' ITR is carried out by ligation of the EcoRI/HindIII fragments obtained from pTG14328 and pTG 14271. The vector thus obtained is called pTG 14330.

The adenoviral genome is then reconstituted by homologous recombination between the HindIII fragment of pTG 14330 and the PacI fragment of pTG 6401. The vector pTG prod 11 is then obtained which is derived from the Ad5 genome deleted for the E1 and E3 regions and contains the 5' and 3' ITRs as well as the encapsidation region of 0.3 kb of BAV3 inserted just upstream of the 3' ITR.

Example 3

Production of Viral Particles

The viral genomes pTG6468 (helper) and pTG6467 or pTG6466 (recombinant) are transfected into the bovine cells of the MBDK line. Next, the transfected cells are infected with a wild-type or attenuated BAV3 genome. Since Ad5 can be propagated in bovine cells in the presence of a BAV3 virus and since the three viral elements contain a BAV3 encapsidation region, they can be packaged into the viral capsids and generate infectious viral particles. The mixture is recovered and a step of amplification by successive cycles of infection of MBDK cells is optionally carried out so as to constitute a viral stock of the three types of virus. During this first step on bovine cells, the BAV3 genome produces trans-acting factors for the encapsidation of the helper vector which provides the viral functions necessary for the propagation of the recombinant vector. The encapsidation of the latter can be mediated by adenoviral factors of BAV3 and Ad5 origin since it possesses the encapsidation regions of both origins and the capsids may contain BAV3 or Ad5 structural proteins.

The viral mixture generated in the bovine line is used to infect human 293 cells. In these cells, the BAV3 virus cannot be propagated even in the presence of Ad5. However, the helper vector of Ad5 origin can replicate its viral genome and express all the early and late viral genes which it carries. On the other hand, it cannot be encapsidated since it is equipped with a single BAV3 encapsidation region. By contrast, the recombinant vector can be encapsidated via the encapsidation region of Ad5 origin and the encapsidation factors provided by the helper vector. The viral particles generated are recovered and can be used for therapeutic purposes.

What is claimed is:

1. An adenoviral vector which is obtained from an adenoviral genome, comprising a cis-acting region essential for encapsidation which is of adenoviral origin and which is heterologous with respect to said adenoviral genome.

2. The adenoviral vector according to claim 1, wherein said adenoviral genome is of human adenovirus origin and wherein said heterologous region essential for encapsidation is of animal adenovirus origin.

3. The adenoviral vector according to claim 2, wherein said adenoviral genome of human origin is of a subgroup C human adenovirus.

4. The adenoviral vector according to claim 1, wherein said heterologous region essential for encapsidation is obtained from an animal adenoviral genome selected from those of canine, avian, bovine, murine, ovine, porcine and simian adenoviruses.

5. The adenoviral vector according to claim 3, wherein said adenoviral genome is of an Ad5 adenovirus and wherein said heterologous region essential for encapsidation is obtained from a bovine adenovirus.

6. The adenoviral vector according to claim 5, wherein said bovine adenovirus is BAV3.

7. The adenoviral vector according to claim 1, wherein said region essential for encapsidation comprises the encapsidation region.

8. The adenoviral vector according to claim 7, wherein said region essential for encapsidation comprises, in addition, the 5' and 3' ITRs.

9. The adenoviral vector according to claim 1, which is defective at least for the E1 function.

10. The adenoviral vector according to claim 9, which is, in addition, defective for at least one of the functions selected from the E2, E3, E4, L1, L2, L3, L4, and L5 functions.

11. The adenoviral vector according to claim 1, which is a helper vector which makes it possible to complement in trans all or part of the defective functions of a recombinant adenoviral vector.

12. The helper adenoviral vector according to claim 11, which comprises 5' and 3' ITR sequences and sequences encoding the functions E2, E4, L1, L2, L3, L4, L5 or combinations thereof obtained from a human adenovirus, and a heterologous encapsidation region obtained from a bovine adenovirus.

13. The helper adenoviral vector according to claim 11, which comprises sequences obtained from a human adenovirus encoding the functions E2, E4, L1, L2, L3, L4, L5 or combinations thereof, and wherein the 5' and 3' ITR sequences and the heterologous encapsidation region are obtained from a bovine adenovirus.

14. The adenoviral vector according to claim 1, which is a recombinant gene transfer vector and comprises at least one gene of interest placed under the control of elements necessary for its expression in a host cell or organism.

15. The recombinant gene transfer adenoviral vector according to claim 14, wherein said gene of interest is selected from genes encoding i) an antisense RNA, ii) a cytokine, iii) a cell or nuclear receptor, iv) a ligand, v) a dystrophin, vi) a growth factor, vii) a coagulation factor, viii) CFTR protein, ix) insulin, x) an enzyme, xi) an enzyme inhibitor, xii) a polypeptide with antitumor effect, xiii) a polypeptide capable of inhibiting a bacterial infection, xiv) a polypeptide capable of inhibiting a parasitic infection, xv) a polypeptide capable of inhibiting a viral infection, xvi) a polypeptide capable of inhibiting HIV, xvii) an antibody, xviii) a toxin, xix) an immunotoxin, xx) an angiogenesis inhibitor, and xxi) a selectable marker.

16. The recombinant gene transfer adenoviral vector according to claim 14, which comprises, in addition, a second encapsidation region which is autologous with respect to the adenovirus genome from which it is obtained.

17. The recombinant gene transfer adenoviral vector according to claim 16, which is defective for all adenoviral functions and comprises, in addition to said gene of interest, at least 5' and 3' ITRs and said autologous encapsidation region which are obtained from a human adenovirus, and said heterologous encapsidation region which is obtained from a bovine adenovirus.

18. The recombinant gene transfer adenoviral vector according to claim 16, wherein the heterologous encapsidation region is inserted 3' of the autologous encapsidation region.

19. A method for complementing all or part of the defective functions of a replication-defective recombinant adenoviral vector, said method comprising introducing into a cell the helper adenoviral vector of claim 11 and the replication-defective recombinant adenoviral vector, wherein said helper adenoviral vector and said replication-defective recombinant adenoviral vector are obtained from the same first adenovirus, and wherein said heterologous region essential for encapsidation carried by the helper vector is obtained from a second adenovirus different from the first adenovirus.

20. The method according to claim 19, wherein said replication-defective recombinant adenoviral vector is a gene transfer vector which comprises a heterologous region essential for encapsidation which is of adenoviral origin and at least one gene of interest placed under the control of elements necessary for its expression in a host cell or organism, and wherein said helper and replication-defective recombinant vectors are obtained from the same first adenovirus and wherein said heterologous regions essential for encapsidation carried by both said helper vector and said replication-defective recombinant vector are obtained from a second adenovirus different from the first adenovirus.

21. A composition comprising:
    (a) a helper adenoviral vector according to claim 11,
    (b) a replication-defective recombinant adenoviral vector, and
    (c) optionally, an adenoviral genome which is obtained from an animal adenovirus of the same origin as the heterologous region essential for encapsidation carried by the vector (a).

22. The composition according to claim 21, wherein said replication-defective recombinant adenoviral vector (b) is a recombinant gene-transfer adenoviral vector comprising a heterologous region essential for encapsidation which is of adenoviral origin and at least one gene of interest placed under the control of elements necessary for its expression in a host cell or organism, and wherein said adenoviral genome
    (c) which is optionally present is obtained from an animal adenovirus which is of the same origin as the heterologous regions essential for encapsidation carried by the vectors (a) and (b).

23. A method for preparing a viral preparation comprising a replication-defective recombinant adenoviral vector, comprising:
    (a) introducing into a first cell line
        (i) a helper adenoviral vector according to claim 11,
        (ii) an adenoviral genome which is obtained from an animal adenovirus, and
        (iii) said replication-defective recombinant adenoviral vector,
    wherein said adenoviral genome (ii) is of the same origin as the heterologous region essential for encapsidation which is carried by the vector (i) and said adenoviral genome (ii) and the vectors (i) and (iii) are capable of replicating in said first cell line,
    (b) culturing said first cell line under appropriate conditions to allow the production of viral particles comprising the vectors (i) and (iii) and the adenoviral genome (ii),
    (c) recovering said viral particles obtained in step (b) from the cell culture,
    (d) infecting a second cell line with said viral particles recovered in step (c), said helper vector (i) and said adenoviral genome (ii) having a reduced encapsidation capacity, a reduced replication capacity, or both reduced encapsidation and replication capacities in said second cell line,
    (e) culturing said second cell line under appropriate conditions to allow the encapsidation of said recombinant adenoviral vector (iii) and produce said viral preparation, and
    (f) recovering said viral preparation obtained in step (e) from the cell culture.

24. The method according to claim 23, wherein said replication-defective recombinant adenoviral vector (iii) comprises a heterologous region essential for encapsidation which is of adenoviral origin, and wherein said adenoviral genome (ii) is of the same origin as the heterologous regions essential for encapsidation carried by the vectors (i) and (iii) and said adenoviral genome (ii), and the vectors (i) and (iii) are capable of replicating in said first cell line.

25. The method according to claim 24, according to which there are introduced into said first cell line:
    the helper adenoviral vector (i) according to claim 11 is defective at least for the E1 function,
    the adenoviral genome (ii) obtained from a bovine adenovirus, and
    the recombinant adenoviral vector (iii) is defective for the E1 function and at least one of the E2, E4, L1, L2, L3, L4, or L5 functions, and wherein said first cell line is of bovine origin.

26. The method according to claim 23, wherein said adenoviral genome (ii) is defective for the E1 function and said first cell line is a cell for complementing the E1 function of said adenoviral genome (ii).

27. The method according to claim 26, wherein said first cell line is obtained from an MDBK line or from primary bovine cells of the retina or fetal kidney and comprises sequences encoding the E1 region of a bovine adenovirus, which are placed under the control of the elements necessary for their expression.

28. The method according to claim 23, wherein said second cell line is a cell for complementing the E1 function of a human adenovirus.

29. The method according to claim 28, wherein said second cell line is the 293 line.

30. A viral preparation obtained according to the method of claim 24, said viral preparation being recovered in step (f) of said method.

31. The viral preparation according to claim 30, comprising at least 30% of infectious viral particles containing said replication-defective recombinant adenoviral vector.

32. A host cell comprising an adenoviral vector according to claim 14.

33. A cell comprising:
    (i) a helper adenoviral vector according to claim 11, and
    (ii) an adenoviral genome which is obtained from an animal adenovirus,
wherein said adenoviral genome which is obtained from an animal adenovirus complements some or all defective functions of said helper adenoviral vector.

34. The cell according to claim 33 further comprising a replication-defective recombinant adenoviral vector.

35. A host cell infected with the viral preparation of claim 30.

* * * * *